United States Patent
Sherman (10) Patent No.: US 8,146,595 B2
(45) Date of Patent: Apr. 3, 2012

(54) ADJUSTABLE PATIENT INTERFACE FOR A BREATHING ASSISTANCE SYSTEM

(75) Inventor: Benjamin Sherman, Milpitas, CA (US)

(73) Assignee: Nellcor Puritan Bennett LLC, Boulder, CO (US)

(*) Notice: Subject to any disclaimer, the term of this patent is extended or adjusted under 35 U.S.C. 154(b) by 1259 days.

(21) Appl. No.: 11/469,216

(22) Filed: Aug. 31, 2006

(65) Prior Publication Data
US 2008/0072909 A1    Mar. 27, 2008

(51) Int. Cl.
*A62B 18/08* (2006.01)
*A62B 18/02* (2006.01)

(52) U.S. Cl. ......... 128/206.24; 128/206.21; 24/DIG. 48

(58) Field of Classification Search ............. 128/205.25, 128/206.24, 207.11, 206.26, 202.27, 207.13, 128/206.27, 206.21; 24/593.11, 595.1, 596.1, 24/DIG. 48; 292/42, 101, 137, 162, 175, 292/145, 300; 403/105
See application file for complete search history.

(56) References Cited

U.S. PATENT DOCUMENTS

| | | | | |
|---|---|---|---|---|
| 2,877,764 A * | 3/1959 | Galleher, Jr. | ............ | 128/206.24 |
| 3,040,741 A * | 6/1962 | Carolan | .................. | 128/206.27 |
| 5,074,297 A | 12/1991 | Venegas | .................. | 128/204.18 |
| 5,921,239 A | 7/1999 | McCall et al. | ............ | 128/205.25 |
| 6,185,791 B1 | 2/2001 | Khokhar | ............................ | 24/16 |
| 6,397,847 B1 | 6/2002 | Scarberry et al. | ........ | 128/206.24 |
| 6,412,487 B1 | 7/2002 | Gunaratnam et al. | ... | 128/206.24 |
| 6,497,756 B1 * | 12/2002 | Curado et al. | ............... | 96/117.5 |
| 6,530,373 B1 | 3/2003 | Patron et al. | ............. | 128/205.25 |
| 7,503,327 B2 * | 3/2009 | Gunaratnam | ........... | 128/206.24 |
| 2003/0075180 A1 | 4/2003 | Raje et al. | ................ | 128/206.24 |
| 2003/0089372 A1 | 5/2003 | Frater et al. | ............. | 128/206.24 |
| 2005/0268914 A1 * | 12/2005 | Paoluccio et al. | ........ | 128/205.25 |
| 2005/0283884 A1 * | 12/2005 | Poole | ................. | 2/410 |
| 2006/0032504 A1 * | 2/2006 | Burton et al. | ............ | 128/207.11 |
| 2006/0076019 A1 * | 4/2006 | Ho | ............................ | 128/206.24 |
| 2006/0118117 A1 * | 6/2006 | Berthon-Jones et al. | | 128/206.21 |
| 2007/0044804 A1 * | 3/2007 | Matula et al. | ............ | 128/206.21 |

FOREIGN PATENT DOCUMENTS

WO    WO 2004/071565 A1    8/2004
WO    WO 2005/118042 A2    12/2005

OTHER PUBLICATIONS

International Search Report and Written Opinion PCT/US2007/077192, 17 pages, Feb. 29, 2008.

* cited by examiner

*Primary Examiner* — Justine Yu
*Assistant Examiner* — Rachel Young (57) ABSTRACT

An adjustable patient interface for a breathing assistance system may include a shell portion and a cushion portion. The shell portion may include one or more shell connection portions. The cushion portion may include a face contacting portion configured to contact a patient's face, and an adjustment portion including one or more cushion connection portions. Each cushion connection portion may correspond to a region of the face contacting portion. Each cushion connection portion may be configured to interact with a corresponding shell connection portion such that a particular cushion connection portion may be manually adjusted relative to a particular shell connection portion to adjust the distance between a region of the face contacting portion corresponding to the particular cushion connection portion and the shell portion.

25 Claims, 4 Drawing Sheets

ADJUSTABLE PATIENT INTERFACE FOR A BREATHING ASSISTANCE SYSTEM

TECHNICAL FIELD

The present disclosure relates generally to the field of breathing assistance systems, e.g., an adjustable patient interface for a breathing assistance system.

BACKGROUND

In recent years, continuous positive airway pressure (CPAP) therapy has become a common prescription for individuals suffering from sleep apnea and/or other breathing ailments. Such therapy may involve placement of a nose or face mask on the subject during sleeping, while positive pressure air is continuously delivered to the subject through the mask. The positive pressure air may be delivered to the patient's upper airway via a face mask or other patient interface in order to prevent the upper airway tissues from collapsing during sleep, thus reducing the occurrence and/or severity of sleep apnea.

SUMMARY

In accordance with one embodiment of the disclosure, an adjustable patient interface for a breathing assistance system may include a shell portion and a cushion portion. The shell portion may include one or more shell connection portions. The cushion portion may include a face contacting portion configured to contact a patient's face, and an adjustment portion including one or more cushion connection portions. Each cushion connection portion may correspond to a region of the face contacting portion. Each cushion connection portion may be configured to interact with a corresponding shell connection portion such that a particular cushion connection portion may be manually adjusted relative to a particular shell connection portion to adjust the distance between a region of the face contacting portion corresponding to the particular cushion connection portion and the shell portion.

In accordance with another embodiment of the disclosure, an adjustable patient interface for a breathing assistance system may include a cushion configured to contact a patient's face, the cushion having a perimeter, a shell configured to support the cushion, a cushion adjustment system for adjusting the shape of the cushion. The cushion adjustment system may include a plurality of adjustment elements disposed at locations along the perimeter of the cushion. Each adjustment element may be configured to allow manual adjustment of a distance between a region of the cushion corresponding to that adjustment element and the shell.

In accordance with another embodiment of the disclosure, an adjustable cushion for a breathing assistance system may include a face contacting portion configured to contact a patient's face, and an adjustment portion including one or more cushion connection portions configured to interact with one or more shell connection portions of a shell to adjustably couple the cushion to the shell. Each cushion connection portion may correspond to a region of the face contacting portion. A particular cushion connection portion may be manually adjusted relative to a particular shell connection portion to adjust the distance between a region of the face contacting portion corresponding to the particular cushion connection portion and the shell.

In accordance with another embodiment of the disclosure, a mask assembly having an adjustable patient interface for use in a breathing assistance system may include one or more gas delivery conduits, an adjustable patient interface, and a headgear. The one or more gas delivery conduits may be configured to receive gas from a gas delivery source. The adjustable patient interface may be configured to communicate gas from the one or more gas delivery conduits to a patient. The adjustable patient interface may include a shell including one or more shell connection portions, and a cushion including a face contacting portion configured to contact the patient's face and an adjustment portion including one or more cushion connection portions. Each cushion connection portion may correspond to a region of the face contacting portion. Each cushion connection portion may be configured to interact with a corresponding shell connection portion such that a particular cushion connection portion may be manually adjusted relative to a particular shell connection portion to adjust the distance between a region of the face contacting portion corresponding to the particular cushion connection portion and the shell. The headgear may be coupled to at least one of the adjustable patient interface and the gas delivery conduits and configured to secure the cushion against the patient's face.

In accordance with another embodiment of the disclosure, a method for adjusting a patient interface for a breathing assistance system may include holding a patient interface including: a cushion configured to contact a patient's face, the cushion having a perimeter; a shell configured to support the cushion; and a cushion adjustment system including a plurality of adjustment elements corresponding to different regions of the cushion located along the perimeter of the cushion. Each adjustment element may be positioned in a first position relative to the shell such that each region of the cushion is located at a particular distance from the shell. The method may further include manually adjusting the shape of the cushion by moving one or more particular adjustment elements from the first position relative to the shell to a second position relative to the shell to adjust the distances between the regions of the cushion corresponding to the one or more particular adjustment elements and the shell.

In accordance with another embodiment of the disclosure, an adjustable patient interface for a breathing assistance system may include face contacting means for interfacing with a patient's face, the face contacting means having a perimeter, support means for supporting the face contacting means, and adjustment means for adjusting the shape of the face contacting means. The adjustment means may include a plurality of adjustment elements disposed at locations along the perimeter of the face contacting means. Each adjustment element may be configured to allow manual adjustment of a distance between a region of the face contacting means corresponding to that adjustment element and the support means.

BRIEF DESCRIPTION OF THE DRAWINGS

FIG. 4 is a three-dimensional partial view illustrating the relationship between the cushion connection portion (or tab)

and shell connection portion of the adjustable patient interface of FIGS. 2A-2B, according to another example embodiment.

DETAILED DESCRIPTION OF THE DRAWING

Selected embodiments of the disclosure may be understood by reference, in part, to FIGS. 1-5, wherein like numbers refer to same and like parts. The present disclosure relates generally to adjustable patient interfaces for breathing assistance systems (e.g., ventilators, CPAP devices, or BiPAP devices). In some embodiments, a patient interface assembly includes a shell portion adjustably coupled to a cushion portion such that regions of the cushion portion may be manually adjusted to be closer to or further from the shell portion. For example, the shell portion may include shell connection portions and the cushion portion may include a face contacting portion and an adjustment portion. The adjustment portion may include cushion connection portions configured to be slidably (or otherwise) adjusted relative to corresponding shell connection portions of the shell in order to adjust the distance between particular regions of the face contacting portion and the shell portion. Thus, the three-dimensional contour of the face contacting portion of the cushion portion may be adjusted as desired.

Figure 1:
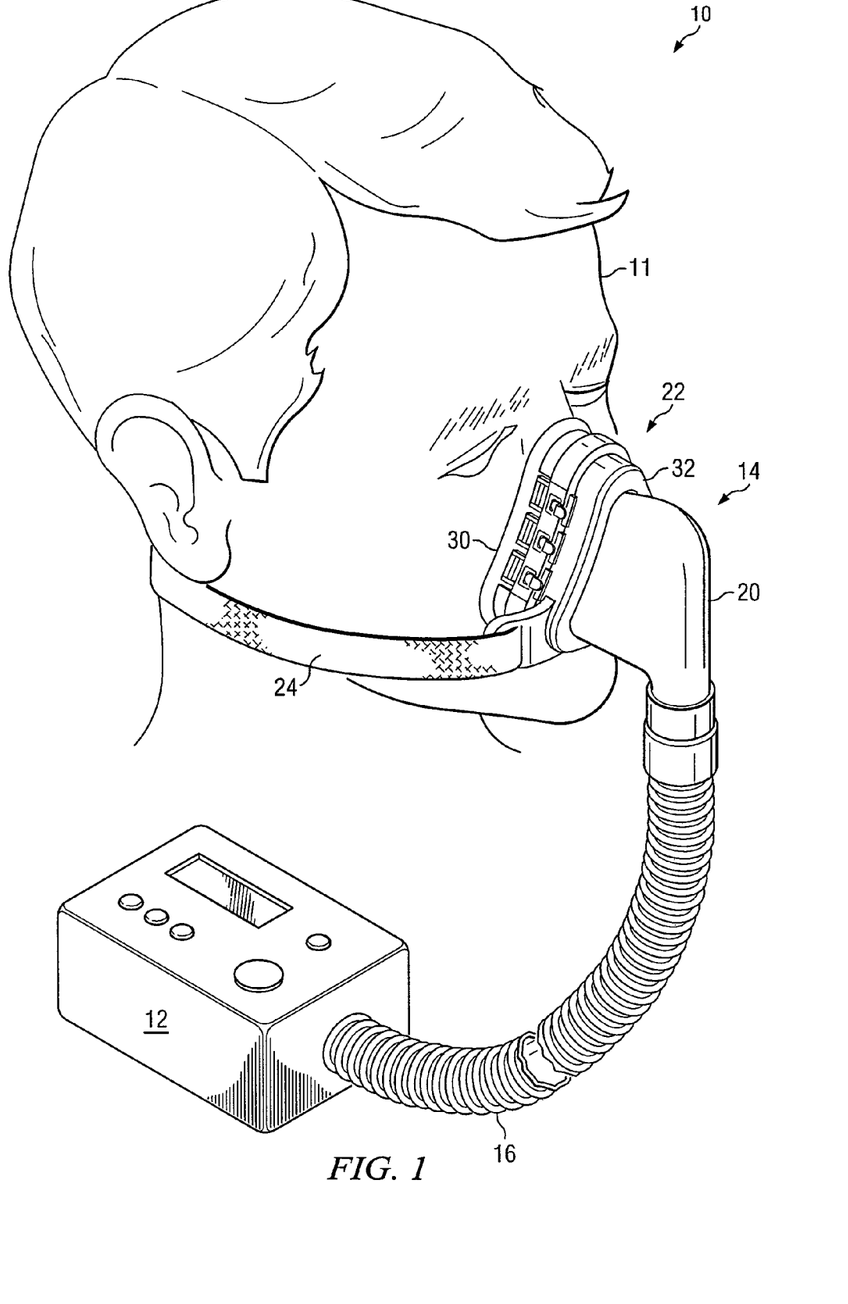
FIG. 1 illustrates an example breathing assistance system, including an adjustable patient interface, for providing breathing assistance to a patient, according to one embodiment of the disclosure.

FIG. 1 illustrates an example breathing assistance system 10 having an adjustable patient interface, according to one embodiment of the disclosure. Breathing assistance system 10 may be generally configured to provide breathing assistance (e.g., providing ventilation and/or treating an apnea or other breathing condition) to a patient 11. Breathing assistance system 10 may include a gas delivery system 12, a mask apparatus 14, and a connection system 16 between gas delivery system 12 and mask apparatus 14.

Gas delivery system 12 may include any device or devices configured to generate, supply, and/or deliver gas (e.g., pressurized air) toward patient 11 via mask apparatus 14. For example, gas delivery system 12 may comprise a device capable of generating pressurized air (e.g., a ventilator, CPAP system, or BiPAP system), a wall outlet through which pressurized air may be supplied (e.g., in a hospital or clinic), one or more tanks of compressed gas, a compressor, or any other suitable source of pressurized or non-pressurized gas. As used herein, the term "gas" may refer to any one or more gases and/or vaporized substances suitable to be delivered to and/or from a patient via one or more breathing orifices (e.g., the nose and/or mouth), such as air, nitrogen, oxygen, any other component of air, $CO_2$, vaporized water, vaporized medicines, and/or any combination of two or more of the above, for example. The term "patient" may refer to any person or animal that may receive breathing assistance from system 10, regardless of the medical status, official patient status, physical location, or any other characteristic of the person. Thus, for example, patients may include persons under official medical care (e.g., hospital patients), persons not under official medical care, persons receiving care at a medical care facility, persons receiving home care, etc.

Mask apparatus 14 may be generally configured to deliver gas supplied by gas delivery system 12 to patient 11 and/or to remove exhaust gas away from patient 11. Mask apparatus 14 may include one or more gas delivery conduits 20, an adjustable patient interface assembly 22 communicatively coupled to at least one conduit 20, and/or headgear 24 for securing mask apparatus 14 to the patient's head, which may include securing patient interface apparatus 22 against the patient's face. Mask apparatus 14 may include any other components, e.g., a forehead support system, one or more adjustment systems, and/or a gas exhaust system, each of which may be separate from, or partially or fully integrated with, one or more other components of mask apparatus 14.

Mask apparatus 14 may be coupled to gas delivery system 12 by connection system 16. Connection system 16 may include any one or more conduits (e.g., one or more flexible hoses) for communicating gas from gas delivery system 12 to mask apparatus 14. In some embodiments, connection system 16 may be coupled to one or more gas delivery conduits 20 of mask apparatus 14. When assembled, breathing assistance system 10 may define one or more gas delivery passageways from gas delivery system 12 to patient 11, passing through connection system 16, gas delivery conduit(s) 20, patient interface assembly 22, and/or one or more other components of system 10. Such passageways may be used to deliver gas from gas delivery system 12 to patient 11. In addition, in some embodiments, gas delivery conduits 20 and/or connection system 16 may include or define one or more passageways for communicating exhaled gas away from patient 11.

As discussed in greater detail with reference to FIGS. 2-4, adjustable patient interface assembly 22 may include a cushion portion 30 adjustably coupled to a shell portion 32 such that the shape of cushion portion 30 may be adjusted to fit patient 11. As discussed below, shell portion 32 may include shell connection portions and cushion portion 30 may include cushion connection portions configured to adjustably couple to corresponding shell connection portions in order to adjust the three-dimensional contour of the cushion portion as desired.

Figure 2A:
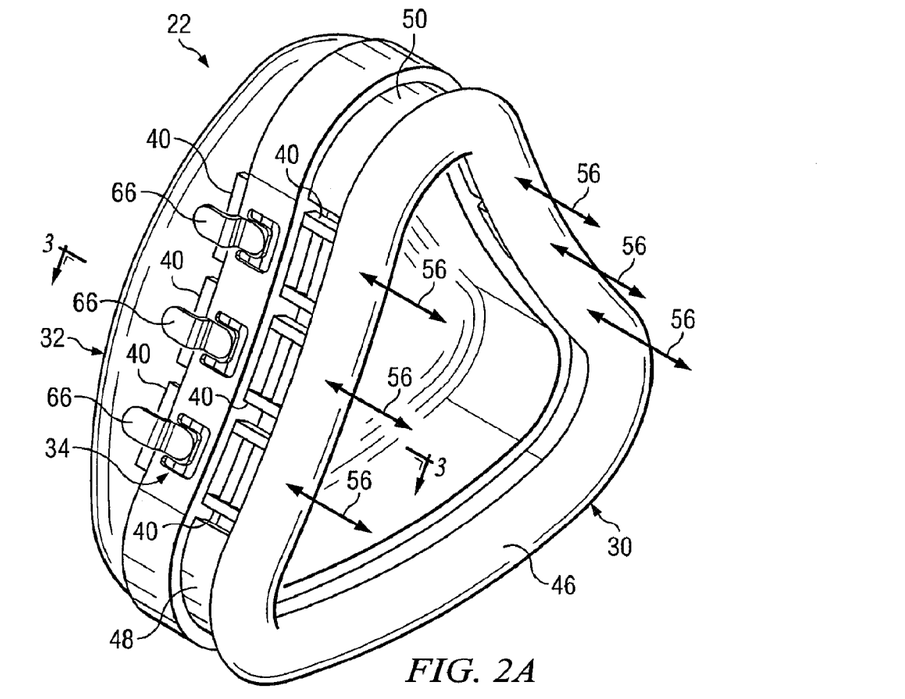
FIGS. 2A and 2B illustrate three-dimensional views of an example adjustable patient interface for use with a breathing assistance system, according to one embodiment.
Figure 2B:
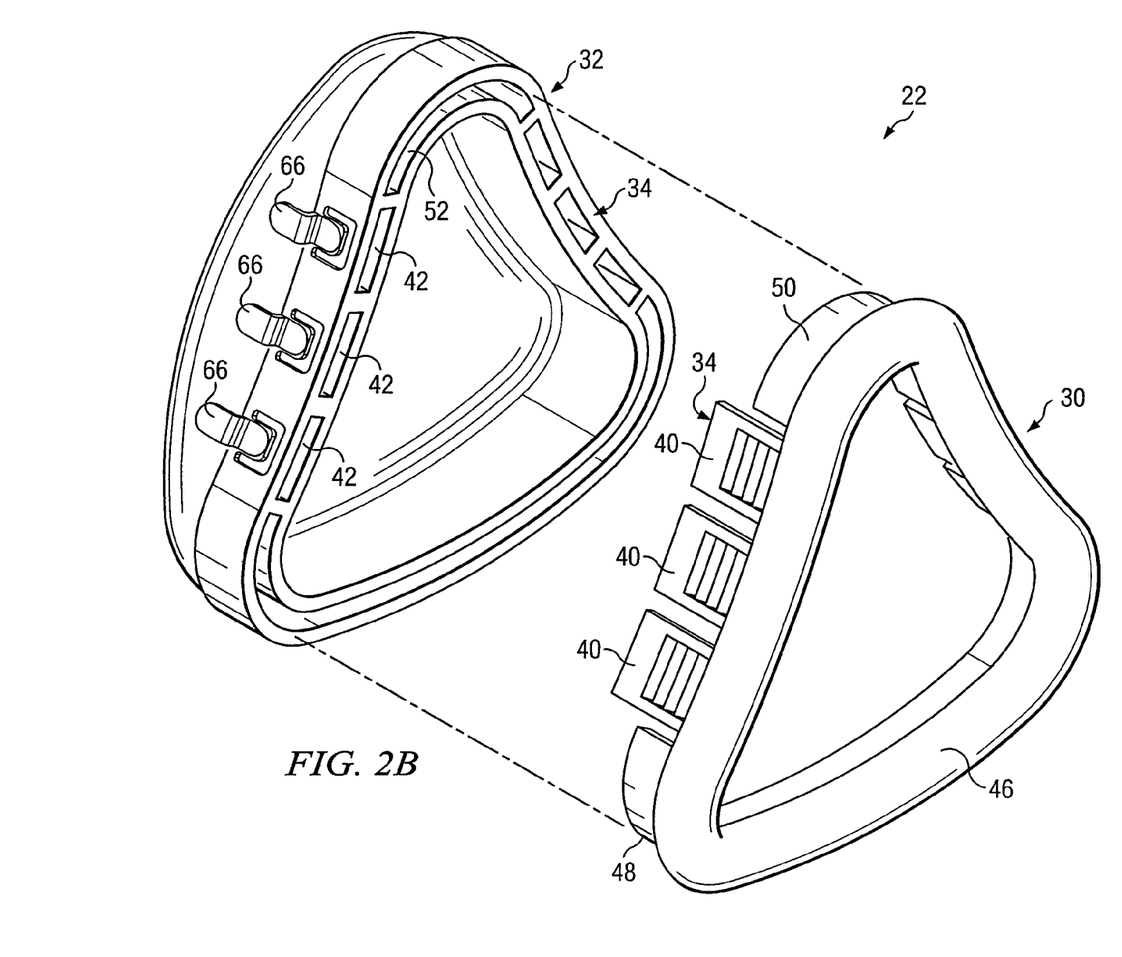

FIGS. 2A and 2B illustrate three-dimensional views of an example patient interface assembly 22 for use with breathing assistance system 10, according to one embodiment. As discussed above, patient interface assembly 22 may include a cushion portion 30 and a shell portion 32. FIG. 2A illustrates cushion portion 30 separate from shell portion 32, while FIG. 2B illustrates cushion portion 30 adjustably coupled to shell portion 32 such that the shape of cushion portion 30 may be adjusted to fit patient 11.

As shown in FIGS. 2A-2B, patient interface assembly 22 may include a cushion adjustment system 34 for adjusting the shape or contour of cushion portion 30. Cushion adjustment system 34 may include adjustment elements coupled to, integrated with, or defined by cushion portion 30 and/or shell portion 32, e.g., as discussed below. Cushion adjustment system 34 may include one or more cushion connection portions 40 associated with cushion portion 30 and one or more shell connection portions 42 associated with shell portion 32. Cushion connection portions 40 and shell connection portions 42 may be configured to interact such that the position and/or shape of particular regions of cushion portion 30 relative to shell portion 32 may be manually adjusted.

In some embodiments, cushion portion 30 may include a cushion (or face contacting portion) 46 and an adjustment portion 48. Cushion 46 may comprise any structure suitable for contacting and/or providing a seal against a patient's face. In some embodiments, cushion 46 may be configured to surround, cover, or interface with the nose and/or the mouth. For example, cushion 46 may comprise a nasal cushion configured to fit around the nose, a mouth cushion configured to fit around the mouth, a face cushion configured to fit around both the nose and mouth, or nasal pillows configured to directly interface with the nostrils.

Cushion 46 may be formed from any suitable materials, e.g., materials suitable for forming a seal with the patient's face. In some embodiments, cushion 46 may be formed from relatively flexible or deformable materials, such as flexible or deformable plastic, rubber, polymer, silicon, or gel, for example. In some embodiments, cushion 46 may have one or more membranes which may be contoured to provide a seal against the patient's face. In other embodiments, cushion 46 may include one or more inflatable portions. Cushion 46 may have any suitable shape and/or cross-section. In some embodiments in which cushion 46 is configured to fit around the patient's nose (e.g., as shown in FIGS. 2A-2B), cushion 46 may have a generally triangular shape.

Adjustment portion 48 may be indirectly or directly coupled to, or integrated with, cushion 46. Adjustment portion 48 may include or define one or more cushion connection portions 40, which may be configured to interact with one or more shell connection portions 42 to adjustably couple cushion portion 30 with shell portion 32, as discussed above. Cushion connection portions 40 may comprise any device or structure configured to interact with shell connection portions 42. For example, cushion connection portions 40 may comprise female connectors, male connectors, clips, tabs, hooks, slots, openings, or any other suitable structures.

Cushion connection portions 40 may be located around a perimeter of cushion 46 and may be spaced at any distance from each other. In addition, cushion connection portions 40 may be separated by one or more support or spacer members or structures 50. In some embodiments, a first set of cushion connection portions 40 are disposed along a first side of cushion 46 configured to fit against the face on one side of the patient's nose, and a second set of cushion connection portions 40 are disposed along a second side of cushion 46 configured to fit against the face on the other side of the patient's nose. For example, one to five cushion connection portions 40 may be disposed along each of the first and second sides of cushion 46. In the example embodiment shown in FIGS. 2A-2B, three cushion connection portions 40 are disposed along each of the first and second sides of cushion 46. In some embodiments, one or more cushion connection portions 40 may be disposed along a portion of cushion 46 configured to fit against the bridge of the nose and/or along a portion of cushion 46 configured to fit against the patient's upper or lower lip.

Shell portion 32 may have any shape and/or configuration suitable to provide support for and/or allow the adjustment of cushion portion 30. For example, in some embodiments, shell portion 32 may have an actual shell-like shape defining an internal volume through which breathing gas may flow, while in other embodiments, shell portion 32 may be a frame or other connection member not having a shell-like shape.

Shell connection portions 42 may comprise any device or structure configured to interact with cushion connection portions 40. For example, shell connection portions 42 may comprise female connectors, male connectors, clips, tabs, hooks, slots, openings, or any other suitable structures. Shell connection portions 42 may be located around a perimeter of shell portion 32 and may be spaced at any distance from each other. In addition, shell connection portions 42 may be separated by one or more support or spacer members or structures 52. In some embodiments, a first set of shell connection portions 42 are disposed along a first side of shell portion 32 configured to be positioned on one side of the patient's nose, and a second set of shell connection portions 42 disposed along a second side shell portion 32 configured to be positioned on the other side of the patient's nose. For example, one to five shell connection portions 42 may be disposed along each of the first and second sides of shell portion 32. In the example embodiment shown in FIGS. 2A-2B, three shell connection portions 42 are disposed along each of the first and second sides of shell portion 32. In some embodiments, one or more shell connection portions 42 may be disposed along a portion of shell portion 32 configured to fit against the bridge of the nose and/or along a portion of shell portion 32 configured to fit against the patient's upper or lower lip.

As discussed above, cushion connection portions 40 are configured to interact with shell connection portion 42. In some embodiments (e.g., the embodiment shown in FIGS. 2A-2B), each cushion connection portion 40 may be configured to interact with a single corresponding shell connection portion 42. In other embodiments, multiple cushion connection portions 40 may be configured to interact with a single shell connection portion 42. In still other embodiments, multiple shell connection portions 42 may be configured to interact with a single cushion connection portion 40.

In some embodiments, each shell connection portion 42 is a slot 42 and each cushion connection portion 40 is a tab 40 configured to slide within a corresponding slot 42 to adjust the shape of cushion 46 proximate that tab 40 relative to shell portion 32. Sliding a particular tab 40 within its corresponding slot 42 (in the direction shown by arrows 56) may operate to alter the distance between the region of cushion 46 corresponding to that particular tab 40 and shell portion 32. Thus, by adjusting various tabs 40 within their corresponding slots 42, the three-dimensional contour of cushion 46 may be adjusted.

In some embodiments, each cushion connection portion 40 may be manually adjusted between and/or releasably locked in a finite number of predetermined positions relative to its corresponding shell connection portion 42. For example, cushion connection portion 40 and/or shell connection portion 42 may include a number of locking members allowing a particular cushion connection portion 40 to be locked in a number of predetermined positions relative to a corresponding shell connection portion 42. In other embodiments, each cushion connection portion 40 may be manually adjusted between and/or releasably locked in an infinite number of positions relative to its corresponding shell connection portion 42.

In the embodiment shown in FIGS. 2A-2B, each cushion connection portion (or tab) 40 includes a number of cushion locking members 60 arranged in a row extending away from cushion 46. Each locking member 60 may provide a distinct position for which that tab 40 may be located within its corresponding slot 42. In this embodiment, cushion locking members 60 may be referred to as teeth 60. Each shell connection portion, or slot, 42 may include a corresponding shell locking member 62 configured to interact with the teeth 60 of a tab 40 in order to releasably lock tab 40 in place relative to that slot 42. As used herein, to "lock" means to prevent or substantially prohibit movement in at least one direction. In this embodiment, each shell locking member 62 may be pivotally coupled to, or pivotally moveable relative to, shell portion 32. As discussed in greater detail below, each shell locking member 62 may include a lever 66 or other device for manually manipulating shell locking member 62 between a locked position and an unlocked position relative to a corresponding tab 40, such that tab 40 may be adjusted in the unlocked position.

Figure 3:
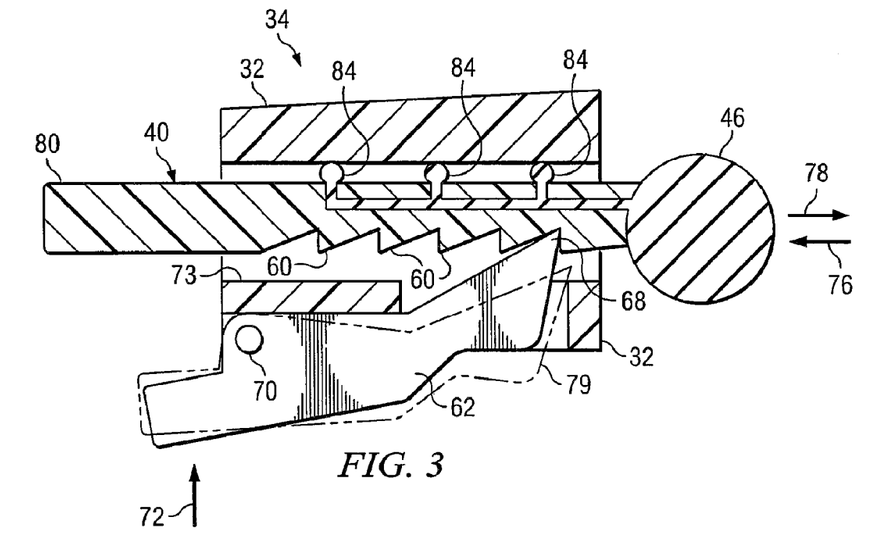
FIG. 3 is a cross-sectional view taken along line A-A illustrating the relationship between a cushion connection portion (or tab) and a shell connection portion of the adjustable patient interface of FIGS. 2A-2B, according to an example embodiment.

FIG. 3 is a cross-sectional view taken along line A-A illustrating the relationship between a cushion connection portion (or tab) 40 and a shell connection portion 42, according to an example embodiment. As discussed above, tab 40 may include a number of teeth 60. Shell locking member 62 may include a tooth 68 projecting inwardly of shell portion 32 and lever 66 projecting inwardly of shell portion 32. Shell locking member 62 may be pivotally connected to shell portion 32 at a pivot point or pivot area 70. In some embodiments, e.g., as shown in FIG. 3, shell locking member 62 is pivotally attached to a wall or other structure of shell portion 32, e.g., wall portion 73. In other embodiments, e.g., as shown in FIGS. 2A, 2B, and 4, shell locking member 62 may be coupled to or integral with a wall or other structure of shell portion 32, e.g., wall portion 73, such that shell locking member 62 and wall portion 73 pivot together relative to the rest of shell portion 32. Lever 66 may be pivotally coupled to shell portion 32 in any other suitable manner. Lever 66 may be manually pressed as indicated by arrow 72 to pivot shell locking member 62 between a locked position (indicated by solid lines in FIG. 3) and an unlocked position (indicated by dashed lines 79 in FIG. 3). In the locked position, tooth 68 may engage with a particular tooth 60 on tab 40 to prevent tab 40 from sliding in the direction indicated by arrow 76, but may allow tab 40 to slide in the opposite direction indicated by arrow 78.

Thus, in this configuration, locking member 62 may prevent cushion 46 (more particularly, the region of cushion 46 corresponding to tab 40) from moving toward shell portion 32. Locking members 62 may thus resist or prevent cushion 46 from collapsing toward shell portion 32, e.g., when patient interface 22 is positioned on the patient's face and a force is applied to shell portion 32 in a direction toward the face. However, even in the locked position of locking member 62, cushion 46 may be adjusted away from shell portion 32 by pressing an end portion 80 of tab 40 in the direction indicated by arrow 78.

In the unlocked position of locking member 62, tooth 68 may be disengaged from teeth 60 to allow tab 40 to slide in both directions 76 and 78. Thus, in order to adjust cushion 46 (more particularly, the region of cushion 46 corresponding to tab 40) closer to shell portion 32, a user may manually press lever 66 as indicated by arrow 72 to unlock locking member 62, and press cushion 46 in the direction indicated by arrow 76.

As shown in FIG. 3, cushion 46 may be disposed at least partially within openings formed in tab 40 such that cushion 46 is coupled to tab 40. Cushion 46 may be inserted into such openings in tab 40, formed integrally with tab 40, or otherwise coupled with tab 40. In this embodiment, cushion 46 may include one or more sliding members 84 projecting from one or more sides of tab 40 in order to (a) provide a seal between tab 40 and one or more walls or other structures of shell portion 32 (e.g., to reduce or prevent gas flow between the inside of patient interface 22 and the outside environment) and/or (b) reduce friction between tab 40 and one or more walls or other structures of shell portion 32. Sliding members 84 may be formed of any suitable sealing and/or low-friction material (e.g., silicon or rubber), which may or may not be the same material as the remainder of cushion 46.

In other embodiments, cushion 46 and tab 40 may be coupled to or integrated with each other in any other suitable or known manner. As examples only, cushion 46 and tab 40 may be coupled using fasteners or adhesives or may be overmolded together.

Figure 4:
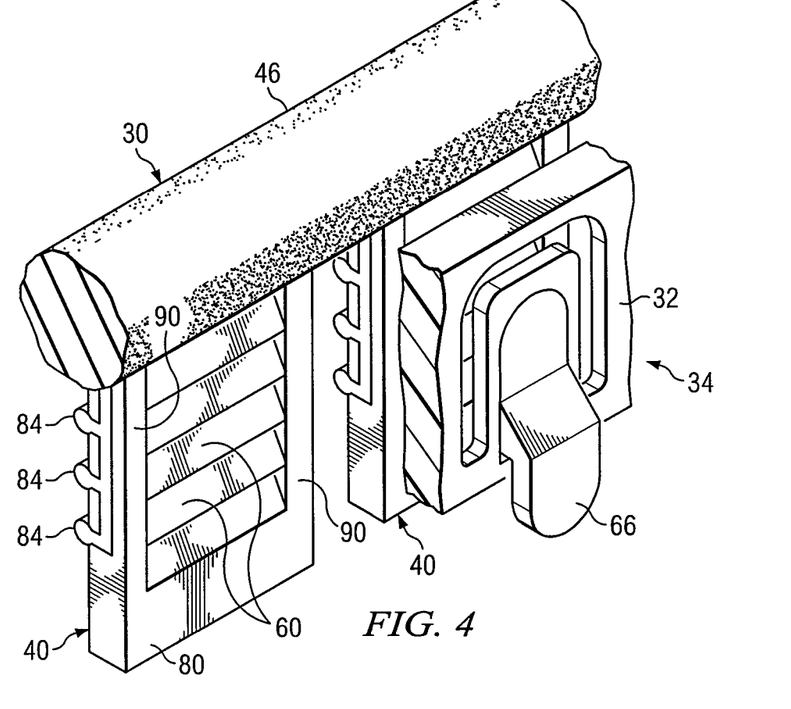

FIG. 4 is a three-dimensional partial view illustrating the relationship between a shell connection portion 42 and a cushion connection portion (or tab) 40, according to an example embodiment. Cushion locking members (or teeth) 60 formed on tab 40 may be supported between a pair of sidewalls 90. As discussed above regarding FIG. 3, cushion 64 may include sliding members 84 projecting from tab 40.

Figure 5:
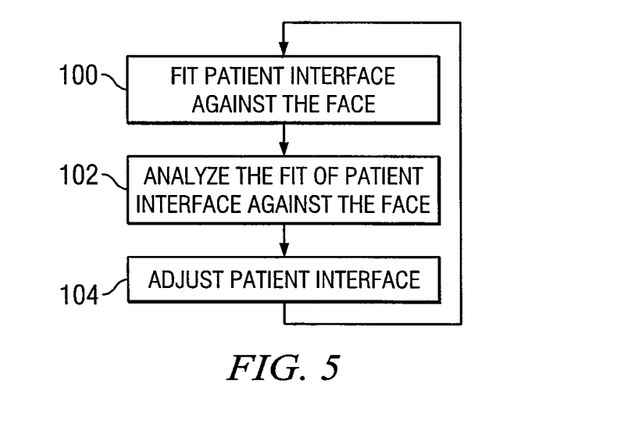
FIG. 5 illustrates a method for adjusting the patient interface of FIGS. 2A-2B to fit against a patient's face, according to one embodiment.

FIG. 5 illustrates a method for adjusting patient interface 22 to fit against a patient's face, according to one embodiment. At step 100, patient 11 may position patient interface 22 against his face such that cushion 46 contacts the face. For example, patient 11 may secure mask apparatus 14 to his head or simply holding patient interface 22 against the face without securing mask apparatus 14 to the head.

At step 102, patient 11 may analyze the fit of patient interface 22 against his face, which may include, e.g., analyzing the comfort of cushion 46 against the face and/or analyzing leak paths between cushion 46 and the face. In some instances, patient 11 may operate system 10 to deliver gas through patient interface 22 in order to check for leaks between cushion 46 and the face.

At step 104, patient 11 may adjust the shape or contour of cushion 46 using cushion adjustment system 34. For example, patient 11 may adjust one or more cushion connection portions 40 relative to corresponding shell connections portions 42, e.g., as described above, in order to adjust the distance between particular region(s) of cushion 46 and shell portion 32. The method may then return to step 100 such that patient may re-fit patient interface 22 against his face and, if necessary, make further adjustments.

It will be appreciated that while the disclosure is particularly described in the context of breathing assistance systems, the apparatuses, techniques, and methods disclosed herein may be similarly applied in other contexts. Additionally, it should be understood that various changes, substitutions and alterations can be made herein without departing from the spirit and scope of the disclosure as illustrated by the following claims.

What is claimed:

1. An adjustable patient interface for a breathing assistance system, comprising:
   a shell portion including one or more shell connection portions;
   at least one shell connection portion comprising a substantially rectangular slot; and
   a cushion portion including:
      a face contacting portion configured to contact a patient's face;
      an adjustment portion including one or more cushion connection portions;
      at least one cushion connection portion comprising a substantially rectangular tab;
      wherein each cushion connection portion corresponds to a region of the face contacting portion; and
      wherein each substantially rectangular tab is configured to interact with a corresponding substantially rectangular slot such that a particular substantially rectangular tab may be manually adjusted between and releasably locked in a plurality of predetermined positions relative to a particular substantially rectangular slot to adjust the distance between a region of the face contacting portion corresponding to the particular substantially rectangular tab and the shell portion; and
      a seal between each substantially rectangular tab and corresponding substantially rectangular slot, the seal configured to reduce or prevent gas flow between an area inside the patient interface and an area outside the patient interface.

2. A patient interface according to claim 1, wherein the particular substantially rectangular tab may be manually adjusted between and releasably locked in the plurality of predetermined positions relative to the particular substantially rectangular slot, without replacing or exchanging any component of the patient interface.

3. A patient interface according to claim 1, wherein:
manually adjusting the particular substantially rectangular tab relative to the particular substantially rectangular slot comprises sliding the particular substantially rectangular tab a distance into or out of the particular substantially rectangular slot.

4. A patient interface according to claim 1, wherein:
the particular substantially rectangular tab comprises a plurality of cushion locking members; and
the particular substantially rectangular slot comprises one or more shell locking members configured to selectively interlock with the plurality of cushion locking members of the substantially rectangular tab.

5. A patient interface according to claim 1, wherein:
the particular substantially rectangular tab includes one or more cushion locking members; and
the particular substantially rectangular slot includes one or more shell locking members configured to interlock with the at least one of the cushion locking members;
wherein adjusting the distance between the region of the face contacting portion corresponding to the particular substantially rectangular tab and the shell portion comprises adjusting the position of the one or more cushion locking members relative to the one or more shell locking members.

6. A patient interface according to claim 1, wherein:
the particular substantially rectangular tab includes a plurality of cushion locking members; and
the particular substantially rectangular slot includes a shell locking member configured to interlock with one of the cushion locking members to prevent movement of the particular substantially rectangular tab relative to the particular substantially rectangular slot in a first direction but not in a second direction generally opposite the first direction.

7. A patient interface according to claim 6, wherein the shell locking member is configured to be moved from a lock position to a unlock position to allow movement of the particular substantially rectangular tab relative to the particular substantially rectangular slot in the first direction.

8. A patient interface according to claim 6, wherein the shell locking member is generally pivotally coupled to the shell portion.

9. A patient interface according to claim 1, wherein:
the face contacting portion is formed from a first, generally flexible material; and
the adjustment portion is formed from a second material more rigid than the first material.

10. A patient interface according to claim 1, wherein the face contacting portion is at least partially disposed within the adjustment portion.

11. A patient interface according to claim 1, wherein:
the face contacting portion defines a first side configured to interface with the face on a first side of the nose and a second side configured to interface with the face on a second side of the nose; and
the adjustment portion includes between one and five cushion connection portions corresponding to the first side of the face contacting portion and one and five cushion connection portions corresponding to the second side of the face contacting portion.

12. An adjustable patient interface for a breathing assistance system, comprising:
a cushion configured to contact a patient's face, the cushion having a perimeter;
a shell configured to support the cushion; and
a cushion adjustment system for adjusting the shape of the cushion, the cushion adjustment system including a plurality of adjustment elements disposed at locations along the perimeter of the cushion, each adjustment element configured to allow manual adjustment of a distance between a region of the cushion corresponding to that adjustment element and the shell without replacing or exchanging any component of the cushion adjustment system;
wherein the shell includes a plurality of connection portions configured to interface with an adjustment element;
a particular adjustment element includes a plurality of cushion locking members; and
a particular connection portion includes a shell locking member configured to interlock with one of the cushion locking members to prevent movement of the particular adjustment element relative to the particular connection portion in a first direction but not in a second direction generally opposite the first direction; and
a seal between each shell locking member and corresponding cushion locking members, the seal configured to reduce or prevent gas flow between an area inside the patient interface and an area outside the patient interface.

13. A patient interface according to claim 12, wherein each adjustment element may be manually adjusted between a number of predetermined positions relative to the shell.

14. A patient interface according to claim 12, wherein each adjustment element may be releasably locked in one of a number of predetermined positions relative to the shell.

15. A patient interface according to claim 12, wherein:
the shell includes a plurality of slots configured to receive the plurality of adjustment elements; and
manual adjustment of a distance between a region of the cushion corresponding to an adjustment element and the shell comprises sliding a particular adjustment element a distance into or out of a particular slot.

16. A patient interface according to claim 12, wherein the shell locking member is configured to be moved from a lock position to a unlock position to allow movement of the particular adjustment element relative to the particular connection portion in the first direction.

17. A patient interface according to claim 12, wherein the shell locking member is generally pivotally coupled to the shell.

18. A patient interface according to claim 12, wherein the cushion includes:
a face contacting portion configured to contact a patient's face, the face contacting portion formed from a first, generally flexible material; and
an adjustment portion including the one or more adjustment elements, the adjustment portion formed from a second material more rigid than the first material.

19. A patient interface according to claim 12, wherein:
the cushion defines a first side configured to interface with the face on a first side of the nose and a second side configured to interface with the face on a second side of the nose; and
the cushion adjustment system includes between one and five adjustment elements corresponding to the first side of the cushion and one and five adjustment elements corresponding to the second side of the cushion.

20. An adjustable breathing assistance system, comprising:
a cushion including:
a face contacting portion configured to contact a patient's face;

an adjustment portion including one or more cushion connection portions configured to interact with one or more shell connection portions of a shell to adjustably couple the cushion to the shell; and at least one sliding member;

wherein each cushion connection portion corresponds to a region of the face contacting portion; and wherein a particular cushion connection portion may be manually adjusted relative to a particular shell connection portion to adjust the distance between a region of the face contacting portion corresponding to the particular cushion connection portion and the shell without replacing or exchanging any cushion connection portions or shell connection portion; and a seal between each cushion connection portion and corresponding shell connection portion, the seal configured to reduce or prevent gas flow between an area inside the patient interface and an area outside the patient interface.

21. A method for adjusting a patient interface for a breathing assistance system, comprising:

holding a patient interface including:
- a cushion configured to contact a patient's face, the cushion having a perimeter;
- a shell configured to support the cushion; and
- a cushion adjustment system including a plurality of adjustment elements corresponding to different regions of the cushion located along the perimeter of the cushion, each adjustment element being positioned in a first position relative to the shell such that each region of the cushion is located at a particular distance from the shell; and
- a seal provided for each adjustment element, the seals configured to reduce or prevent gas flow between an area inside the patient interface and an area outside the patient interface;

manually activating a lever in a first direction such that at least one adjustment element may be manually adjusted in a second direction generally perpendicular to the first direction; and manually adjusting the shape of the cushion by moving one or more particular adjustment elements from the first position relative to the shell to a second position closer to the shell to adjust a distance between a region of the cushion corresponding to the one or more particular adjustment elements and the shell.

22. An adjustable patient interface for a breathing assistance system, comprising:

face contacting means for interfacing with a patient's face, the face contacting means having a perimeter;

support means for supporting the face contacting means;

adjustment means for adjusting the shape of the face contacting means, the adjustment means including a plurality of adjustment elements disposed at locations along the perimeter of the face contacting means, each adjustment element configured to allow manual adjustment of a distance between a region of the face contacting means corresponding to that adjustment element and the support means without replacing or exchanging any of the adjustment elements;

locking means configured to prevent movement of the face contacting means relative to the support means in a first direction but not in a second direction generally opposite the first direction; and a seal provided for each adjustment element, the seals configured to reduce or prevent gas flow between an area inside the patient interface and an area outside the patient interface.

23. A patient interface according to claim 12, wherein the shell locking member comprises at least one tooth configured to interlock with a portion of the cushion locking member.

24. A patient interface according to claim 12, wherein:

the first direction comprises movement of a portion of the cushion toward a portion of the shell; and the second direction comprises movement of the portion of the cushion away from the portion of the shell.

25. An adjustable breathing assistance system according to claim 20, wherein the at least one sliding member is configured to reduce friction between at least one adjustment portion and a corresponding shell connection portion.

* * * * *